(12) United States Patent
Steer

(10) Patent No.: US 12,181,537 B2
(45) Date of Patent: Dec. 31, 2024

(54) MAGNETIC POSITIONING SYSTEM

(71) Applicant: CMR SURGICAL LIMITED, Cambridge (GB)

(72) Inventor: William Andrew Steer, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 155 days.

(21) Appl. No.: 17/986,203

(22) Filed: Nov. 14, 2022

(65) Prior Publication Data

US 2023/0152395 A1 May 18, 2023

(30) Foreign Application Priority Data

Nov. 18, 2021 (GB) ...................................... 2116655

(51) Int. Cl.
*G01R 33/02* (2006.01)
*G01B 7/004* (2006.01)

(52) U.S. Cl.
CPC .............. *G01R 33/02* (2013.01); *G01B 7/004* (2013.01)

(58) Field of Classification Search
CPC ........ G01R 33/02; G01B 7/004; A61B 5/062; A61B 2034/2051; A61B 34/02; A61B 34/30; B25J 13/088; B25J 19/027
USPC ....................................................... 324/200
See application file for complete search history.

(56) References Cited

U.S. PATENT DOCUMENTS

| 4,812,812 A * | 3/1989 | Flowerdew | H01Q 1/04 340/854.6 |
| 4,945,305 A | 7/1990 | Blood | |
| 5,377,678 A * | 1/1995 | Dumoulin | A61B 5/06 600/410 |
| 5,646,524 A * | 7/1997 | Gilboa | G01B 7/004 324/207.17 |

(Continued)

FOREIGN PATENT DOCUMENTS

| WO | 9932033 A1 | 7/1999 |
| WO | 2006121740 A2 | 11/2006 |

OTHER PUBLICATIONS

Attivissimo et al., TDM-FDM configuration of electromagnetic tracking system for image-guided surgery devices, 2017 IEEE International Instrumentation and Measurement Technology Conference (I2MTC), Published May 22, 2017 by IEEE, Accessed Apr. 4, 2022 from https://ieeexplore.ieee.org/document/7969719 doi: 10.1109/I2MTC.2017.79696719.

(Continued)

*Primary Examiner* — Christopher P McAndrew
(74) *Attorney, Agent, or Firm* — Lando & Anastasi, LLP

(57) ABSTRACT

Magnetic positioning systems and methods for use in a robotic surgical system are provided. A multi-axis magnetic field source generates a magnetic field by simultaneously exciting a plurality of axes of the multi-axis magnetic field source with respective source signals that are orthogonal to each other over a period, T. A multi-axis magnetic field sensor detects the generated magnetic field. The detected magnetic field is analysed over an analysis interval which is at least as long as the period, T, to resolve the detected magnetic field into components which are due to the plurality of source signals. The components are used to determine one or both of the position and the orientation of the (Continued)

multi-axis magnetic field sensor relative to the multi-axis magnetic field source.

19 Claims, 8 Drawing Sheets

(56) References Cited

U.S. PATENT DOCUMENTS

| | | | | |
|---|---|---|---|---|
| 5,646,525 | A | * | 7/1997 | Gilboa .................... G01C 9/06 324/207.17 |
| 9,377,348 | B2 | * | 6/2016 | Kataoka ............... A61B 5/7217 |
| 9,937,012 | B2 | * | 4/2018 | Hares ..................... A61B 34/30 |
| 11,076,511 | B2 | * | 7/2021 | Ashe ..................... H01F 27/325 |
| 2003/0201767 | A1 | * | 10/2003 | Khalfin .................. G01S 1/024 600/407 |
| 2008/0204004 | A1 | | 8/2008 | Anderson |
| 2017/0135602 | A1 | * | 5/2017 | Izmirli .................... A61B 5/063 |
| 2018/0245953 | A1 | * | 8/2018 | Nishimoto ........... G01D 11/245 |
| 2020/0221612 | A1 | * | 7/2020 | Ashe ................... H01F 27/2823 |

OTHER PUBLICATIONS

Park et al., Technical Review: Electromagnetic Sensor System for Localization of Medical Devices, 2018 IEEE International Conference on Consumer Electronics—Asia (ICCE-Asia), Published [online] Nov. 29, 2018 by IEEE, Accessed on Apr. 4, 2022 from https://ieeexplore.ieee.org/document/8552100 doi: 10.1109/ICCCE-ASIA.2018.8552100.
Product information, NEOSID, Expertise in components, Sep. 7, 2018/p. 1/10, 3D cube antennas for electromagnetic 6DoF tracking systems.
Raab, F. H. et al., Magnetic Position and Orientation Tracking System, IEEE Transactions on Aerospace and Electronic Systems, vol. AES-15, No. 5, Sep. 1979, pp. 709-718.
Silva, M. T. et al., Alternative Analytical Solution for Position and Orientation in Electromagnetic Motion Tracking Systems, WSEAS Transaction on Systems, E-ISSN: 2224-2678, vol. 16, 2017, pp. 225-233.
United Kingdom Combined Search and Examination Report from corresponding United Kingdom Application No. GB2116655.8 dated Apr. 6, 2022.
Notification of Transmittal of the International Search Report and the Written Opinion of the International Searching Authority from corresponding PCT/GB2022/052901 dated Feb. 8, 2023.

* cited by examiner

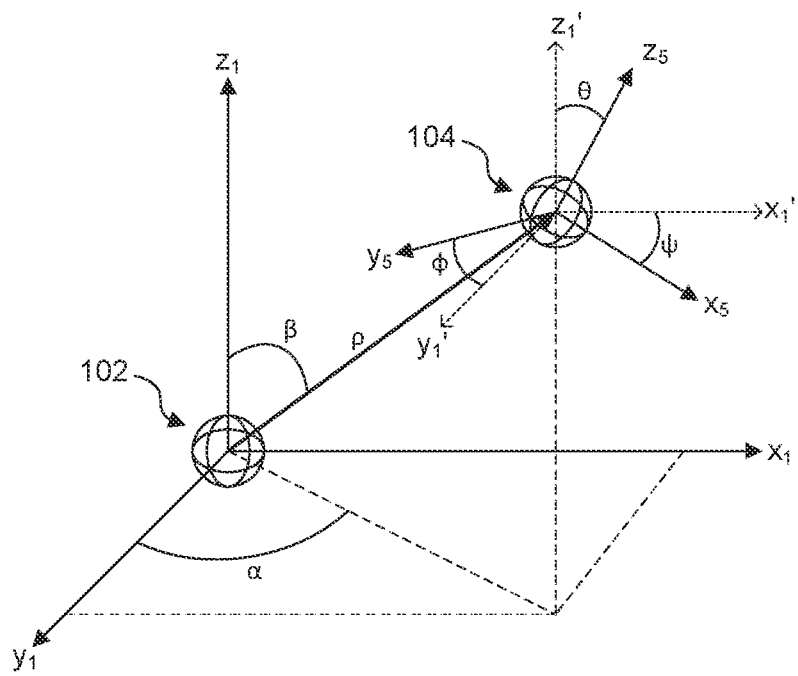
FIGURE 1
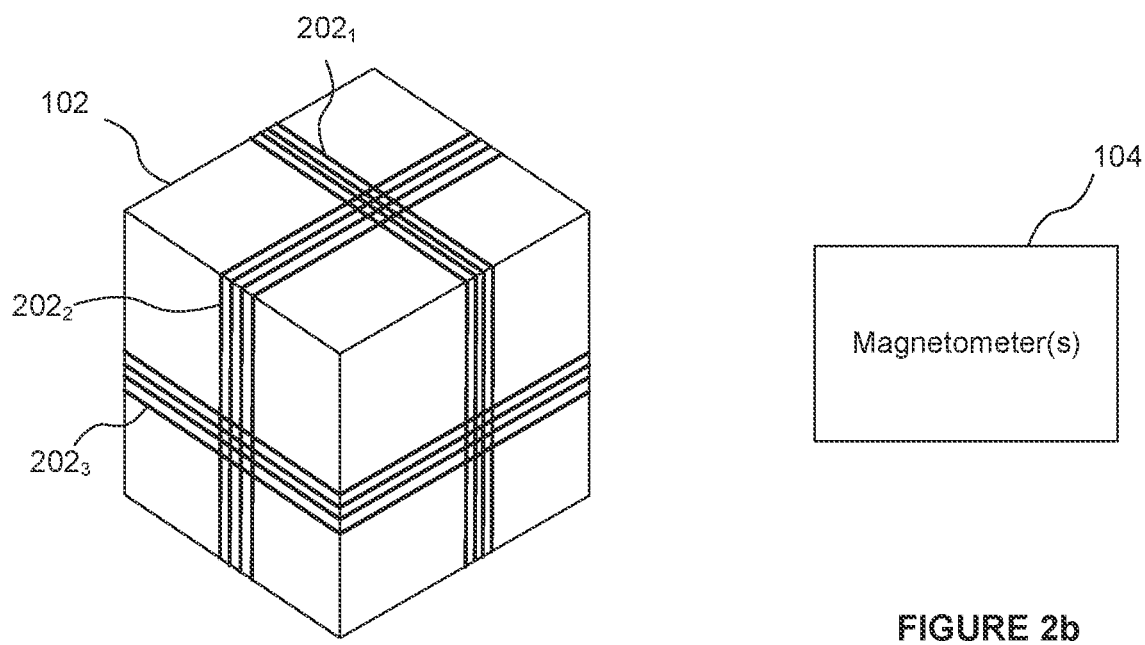
FIGURE 2a
FIGURE 2b

MAGNETIC POSITIONING SYSTEM

CROSS-REFERENCE TO RELATED APPLICATION

This application claims the benefit under 35 U.S.C. § 119 of United Kingdom Patent Application No. 2116655.8 filed on Nov. 18, 2021, which is hereby incorporated herein by reference in its entirety for all purposes.

FIELD

The present application relates to magnetic positioning systems, e.g. magnetic positioning systems which are configured for use with a robotic surgical system.

BACKGROUND

Magnetic positioning systems (which may also be referred to as "electromagnetic (EM) positioning systems") can be used to determine the relative position and/or orientation of components within a space. In this way, a magnetic positioning system can be used to determine the position and orientation of a given object, in relation to a reference frame. A conventional magnetic positioning system comprises a multi-axis magnetic field source which can generate a spatially unique magnetic field by exciting a plurality of its axes. The conventional magnetic positioning system also comprises a multi-axis magnetic field sensor which can detect and analyse the spatially unique magnetic field to determine the relative positions and/or orientations of the source and the sensor. If the multi-axis magnetic field source and the multi-axis magnetic field sensor each have three axes then six degrees of freedom (three degrees of freedom for relative positions and three degrees of freedom for relative orientations) between the source and sensor can be determined. Magnetic positioning systems tend to be appropriate for short-range applications, typically with a maximum distance between the source and the sensor in a range from 30 cm to a few metres, since the magnetic field strength decreases with distance to the third power. One advantage of magnetic positioning methods over other positioning methods, for instance optical tracking, is that they do not require line of sight from the source to the sensor to determine their relative positions and orientations. This is beneficial for a busy environment such as for use with a robotic surgical system in an operating theatre, or "operating room (OR)", where there are many people and equipment (including plastic drapes) that could obstruct the line of sight.

The principles behind how a magnetic positioning system can use a multi-axis magnetic field source and a multi-axis magnetic field sensor to determine the relative positions and/or orientations of the source and the sensor are known in the art. A brief description of these principles is provided here with reference to FIGS. 1, 2a and 2b. FIG. 1 illustrates the position and orientation of a multi-axis magnetic field source 102 and a multi-axis magnetic field sensor 104. The position and orientation of the source 102 are defined by the origin and the directions of the axes labelled $x_1$, $y_1$ and $z_1$ in FIG. 1. The position of the sensor 104 can be represented in spherical coordinates ($\alpha$, $\beta$, $\varphi$ relative to the source 102. The orientation of the sensor 104 is shown with the directions of the axes labelled $x_s$, $y_s$ and $z_s$ in FIG. 1. FIG. 1 also shows a set of axes labelled $x_1'$, $y_1'$ and $z_1'$ which are parallel to the respective axes $x_1$, $y_1$ and $z_1$ defined for the source 102, but have been shifted to have their origin at the position of the sensor 104. The orientation of the sensor 104 relative to that of the source can be represented by Euler angles ($\varphi$, $\theta$, $\psi$) as shown in FIG. 1. Different representations of the orientation may be used, e.g., yaw-pitch-roll or quaternions. The aim of a magnetic positioning system is to determine the relative positions and orientations of the source 102 and the sensor 104, e.g. to determine the parameters $\alpha$, $\beta$, $\rho$, $\varphi$, $\theta$ and $\psi$. The system can track motion by monitoring the position and orientation of the sensor relative to the source over time.

FIG. 2a illustrates a three-axis magnetic field source as an example of the multi-axis magnetic field source 102, and FIG. 2b illustrates a magnetic field sensor implemented as one or more magnetometers, as an example of the multi-axis magnetic field sensor 104. In this example, the source 102 comprises three coils of wire $202_1$, $202_2$ and $202_3$ around three orthogonal axes of the source 102. By exciting N-turns of a coil with a variable current of amplitude I, a magnetic dipole field is created with a magnetic moment, $\mu$, given as $\mu = NI\Omega$, where $\Omega$ is a vector representing the surface area of the coil, wherein the direction of $\Omega$ is aligned with the normal of the surface area of the coil. To give two examples, the sensor 104 could comprise three anisotropic magneto-resistive (AMR) sensors or could comprise three coils of wire around three orthogonal axes of the sensor.

If a coil of the source 102 has a surface area vector $\Omega$ pointing along the $z_1$ axis then the magnitude of the radial and tangential components of the magnetic field generated by that coil of the source 102, $H_r(\rho, \beta)$ and $H_t(\rho, \beta)$, at a point on a circle defined by parameters $\rho$ and $\beta$, are given by the equations:

$$H_r(\rho, \beta) = \frac{\mu}{2\pi\rho^3}\cos(\beta)$$

$$H_t(\rho, \beta) = \frac{\mu}{4\pi\rho^3}\sin(\beta)$$

According to Faraday's law of induction, if a sensor coil is placed in a varying magnetic field (e.g. at the point on the circle defined by parameters $\rho$ and $\beta$), the variations in the magnetic field at that point will induce a current over the sensor coil. The strength of the induced current depends upon the rate of change of the magnetic field as well as the surface area, orientation and number of turns of the sensor coil. Since the strength of the magnetic field experienced by the sensor coil is a function of the relative position between the source 102 and the sensor coil, it is possible to deduce the position of the sensor coil relative to the source (defined by parameters $\rho$ and $\beta$) from the source and sensor currents. If the sensor 104 is implemented as a coil receiver, three concentric coils ($202_1$ to $202_3$) in both the source 102 and the sensor 104 may be used, with their magnetic moments mutually perpendicular. The configurations (e.g. the number of turns of the coils and the surface area of the coils along each axis) of the source 102 and the sensor 104, as well as the source signals which are used to excite the axes of the source, are known parameters in the magnetic positioning system. Using this known information and the detected magnetic field as detected by each of the sensor coils, a person skilled in the art would know how to determine the relative position and orientation between source 102 and sensor 104. The source 102 and the sensor 104 may or may not have the same parameters, such as number of coil turns and surface area. Instead of using a sensor coil to generate an output signal which is proportional to the rate of change of a magnetic field, a DC-sensor magnetometer could be used which would typically give an output signal which is proportional to the instantaneous magnetic field strength.

There are two conventional approaches to implementing electromagnetic position sensing. A first conventional approach is to use an Alternating Current (AC) method that generates a magnetic field by using high frequency (typically in a range from 10 kHz to 60 kHz) source signals to excite all of the axes of the multi-axis magnetic field source at the same time on different frequencies. A multi-axis sensor is used to detect the magnetic field and to determine the relative positions and orientations of the source and the sensor. In order to distinguish between the signals at different frequencies, the magnetic field is measured and analysed (e.g. using narrowband filters and/or synchronous detection techniques over a measurement time which includes hundreds or thousands of cycles of the different signals) so that the signals can be distinguished from each other and from noise in the system. The use of high frequency signals results in short measurement times and high precision (i.e. high signal to noise ratios ("SNR")), but the use of high frequency signals means that the system is affected and distorted by electrically conducting material in the vicinity. When electrically conducting material (e.g. metal, including non-ferrous metal) is in the presence of an alternating magnetic field, eddy currents are produced in the conducting material that distort the magnetic field, which in turn causes spatial distortions in the determined positions and orientations. According to Lenz's law, an eddy current creates a magnetic field that opposes the change in the magnetic field that created it. The strength of these eddy currents increases as the frequency with which the magnetic field varies increases. In particular, 'skin-depth' describes the penetration-depth of time-varying magnetic fields into electrically conducting solids. Induced electric currents from time-varying fields generate eddy currents which oppose the field, and progressively cancel the field as you get deeper into the material. This means that higher-frequency magnetic fields are blocked (if completely enclosed) or distorted (if not enclosed) by thicknesses of metal. A known limitation of AC systems operating at frequencies in the low 10 s of kilohertz (and above) is that they suffer distortions in the presence of common metal objects and structures. As such, high frequency magnetic fields (e.g. having frequencies above 1 kHz) are not used for positioning systems in environments which include significant amounts of metal. There is usually a lot of metal in an OR, e.g. in a surgical robot, so the conventional high frequency AC methods of magnetic positioning are not well suited to this application. There isn't a hard threshold or cut-off between "high" frequency signals and "low" frequency signals, but lower frequencies allow increasingly thicker pieces of metal to be "transparent" to the distortion caused by eddy currents in metal, and in the context of the normal amounts of metal found in an OR in which a robotic surgical system is implemented, "high frequency signals" can be understood to mean signals with frequencies above 1 kHz.

To avoid the distortion caused by eddy currents which are generated in the presence of high frequency magnetic fields (e.g. frequencies above 1 kHz), magnetic fields with lower frequencies (e.g. frequencies below 1 kHz) may be used to implement a magnetic positioning system in an environment which includes significant thicknesses of metal, such as with a surgical robotic system in an OR. However, if the frequencies of the signals in the conventional AC method are reduced below about 1 kHz, the signals at the different frequencies would become difficult to distinguish from each other and from noise in the system.

A second conventional approach is a "switched DC" method, which works by exciting the axes (e.g. the three axes) of the multi-axis magnetic field source sequentially at different times with short pulses of constant current, typically several milliseconds each. There may be of the order of 100 of these short pulses of constant current per second, and on average they are "off" for longer than they are "on", e.g. they may be "off" for more than twice as long as they are "on". A signal having approximately 100 pulses of constant current per second can be considered to be a signal with a frequency of approximately 100 Hz. These frequencies are sufficiently low for the switched DC method to be mostly unaffected by electrically conducting material such as metal in the vicinity because the frequencies are low enough that the eddy currents decay away and cause minimal distortion. For example, after the field is switched the system can wait a couple of milliseconds for the eddy currents to decay before making a corresponding measurement. However, switched DC methods present their own measurement challenges, including interference from slowly changing background magnetic fields (including the earth's field when the receiver is in motion) and sometimes from AC power-line fields at 50/60 Hz. More generally, interference and receiver noise are more difficult to filter out in the switched DC approach than with the high frequency AC approach. Until recently, magnetometers of sufficient sensitivity for use as DC field sensors have been expensive compared to AC coils. Furthermore, since only one axis is excited at a given time in the switched DC method, the total measurement time needs to be longer in order for each separate signal to have a sufficient time for its signal to be strong enough to distinguish it over the noise in the environment. In particular, the effective measurement time for each axis can be no more than one third of the total measurement time, and in practice may be less if some waiting time is required for the field to stabilise and eddy currents to die away. Furthermore, because the measurements for each axis occur in discrete time intervals, interference and noise are unavoidably aliased into the measurement bandwidth.

With both conventional approaches (the high frequency AC approach and the switched DC approach), as the field strength decreases with the third-power of distance, and as the precision inherently decreases with signal strength and worsening signal-to-noise ratio, achieving good precision at longer ranges in an environment surrounded by metal is difficult (e.g. for use with a robotic surgical system). Taking into account the significant amount of metal and electrical parts in a surgical robotic system, neither of the conventional magnetic positioning approaches is well suited for use in such an environment.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

There is provided a magnetic positioning system configured for use with a robotic surgical system, the magnetic positioning system comprising:
  a multi-axis magnetic field source configured to generate a magnetic field by simultaneously exciting a plurality of axes of the multi-axis magnetic field source with respective source signals that are orthogonal to each other over a period, T; and a multi-axis magnetic field sensor configured to detect the generated magnetic field; wherein the magnetic positioning system is configured to:

analyse the detected magnetic field over an analysis interval which is at least as long as the period, T, to resolve the detected magnetic field into components which are due to the plurality of source signals; and use the components to determine one or both of the position and the orientation of the multi-axis magnetic field sensor relative to the multi-axis magnetic field source.

Each of the source signals may have a frequency such that it has a number of cycles, x, in the period, T, wherein $1 \leq x \leq 50$. For example, $3 \leq x \leq 25$. Each of the source signals may have a frequency in a range from 1 Hz to 500 Hz.

The source signals may be sinusoidal.

The source signals may have different frequencies, and each of the source signals may have a frequency such that it has an integer number of cycles in the period, T, such that the source signals are orthogonal to each other over the period, T. The frequencies of the source signals might not be multiples of one another.

The source signals may be modulated with different orthogonal codes, such that the source signals are orthogonal to each other over the period, T.

Two of the source signals may have phases which differ by $$\frac{\pi}{2},$$

such that said two of the source signals are orthogonal to each other over the period, T.

The magnetic positioning system may be configured to resolve the detected magnetic field into components which are due to the plurality of source signals once per update interval, and use the components to determine one or both of the position and the orientation of the multi-axis magnetic field sensor relative to the multi-axis magnetic field source once per update interval, wherein the update interval may be shorter than the analysis interval. The update interval may be less than or equal to the period T.

The multi-axis magnetic field sensor may be configured to determine, for each of a plurality of axes of the multi-axis magnetic field sensor, an axis-specific sensor signal representing the detected magnetic field for that axis. The magnetic positioning system may be configured to analyse the detected magnetic field by processing the axis-specific sensor signals over said analysis interval to resolve the axis-specific sensor signals into said components which are due to the plurality of source signals.

The magnetic positioning system may be configured to process the axis-specific sensor signals by: multiplying the axis-specific sensor signals by a window function to determine windowed axis-specific sensor signals; and processing the windowed axis-specific sensor signals over said analysis interval to resolve the windowed axis-specific sensor signals into said components which are due to the plurality of source signals.

The window function may be a raised cosine function with a period of 2 T, and wherein said analysis interval over which the windowed axis-specific sensor signals are processed may be 2 T.

A respective window function may be used for each update interval, such that the window functions are overlapping in time.

The magnetic positioning system may be configured to implement a Fast Fourier Transform (FFT) or discrete Fourier integrals to analyse the detected magnetic field over the analysis interval to resolve the detected magnetic field into components which are due to the plurality of source signals.

The multi-axis magnetic field source may be configured to simultaneously excite each of the axes with a plurality of source signals, wherein all of the source signals with which all of the axes are excited may be orthogonal to each other over the period, T.

The multi-axis magnetic field source and the multi-axis magnetic field sensor may each have exactly three axes.

The magnetic positioning system may be configured to synchronise the timing of the multi-axis magnetic field source and the multi-axis magnetic field sensor with each other.

The magnetic positioning system may be configured to synchronise the timing of the multi-axis magnetic field source and the multi-axis magnetic field sensor with each other by: providing an out-of-band time-reference signal to the multi-axis magnetic field source and to the multi-axis magnetic field sensor; causing the multi-axis magnetic field source to excite one or more of its axes with a time-reference signal which has a period of 2 T; or causing the multi-axis magnetic field source to simultaneously excite one of its axes with two source signals which have no common periodicity in intervals which are submultiples of the period, T.

The multi-axis magnetic field sensor may comprise a non-coil based, DC-sensitive magnetometer configured to detect the generated magnetic field.

The magnetic positioning system may comprise a plurality of multi-axis magnetic field sources and a plurality of multi-axis magnetic field sensors, wherein each of the multi-axis magnetic field sources may be configured to generate a magnetic field by simultaneously exciting a plurality of axes of the multi-axis magnetic field source with respective source signals, wherein all of the source signals for all of the multi-axis magnetic field sources may be orthogonal to each other over the period, T.

There may be provided a robotic surgical system comprising:

a plurality of parts; and the magnetic positioning system described in the preceding paragraph, wherein a respective one of the multi-axis magnetic field sources and a respective one of the multi-axis magnetic field sensors is secured to each of the parts.

The magnetic positioning system may be configured to:

for each of the parts, analyse the magnetic field detected at the multi-axis magnetic field sensor secured to that part to determine measurement information indicating one or both of the position and the orientation of that multi-axis magnetic field sensor relative to the multi-axis magnetic field sources secured to a plurality of the other parts; and determine the positions and/or orientations of the parts in the robotic surgical system using: (i) pre-determined information indicating, for each of the parts, the positions and orientations on that part at which the multi-axis magnetic field source and the multi-axis magnetic field sensor are secured, and (ii) the determined measurement information for each of the parts.

The magnetic positioning system may be configured to also use known geometrical arrangements of the parts of the robotic surgical system to determine the positions and/or orientations of the parts in the robotic surgical system.

For each of the parts, the respective multi-axis magnetic field source and the respective multi-axis magnetic field sensor may be secured to the part at separated positions.

The parts may be surgical robot arms and/or carts supporting surgical robot arms.

There is provided a magnetic positioning method for use in a robotic surgical system, the magnetic positioning method comprising:

generating a magnetic field by simultaneously exciting a plurality of axes of a multi-axis magnetic field source with respective source signals that are orthogonal to each other over a period, T;

detecting the generated magnetic field at a multi-axis magnetic field sensor;

analysing the detected magnetic field over an analysis interval which is at least as long as the period, T, to resolve the detected magnetic field into components which are due to the plurality of source signals; and using the components to determine one or both of the position and the orientation of the multi-axis magnetic field sensor relative to the multi-axis magnetic field source.

The above features may be combined as appropriate, as would be apparent to a skilled person, and may be combined with any of the aspects of the examples described herein.

BRIEF DESCRIPTION OF THE FIGURES

Examples will now be described in detail with reference to the accompanying drawings in which:

FIG. 1 illustrates the position and orientation of a multi-axis magnetic field source and a multi-axis magnetic field sensor;

FIG. 2a illustrates a three-axis magnetic field source;

FIG. 2b illustrates a three-axis magnetic field sensor;

Figure 3:
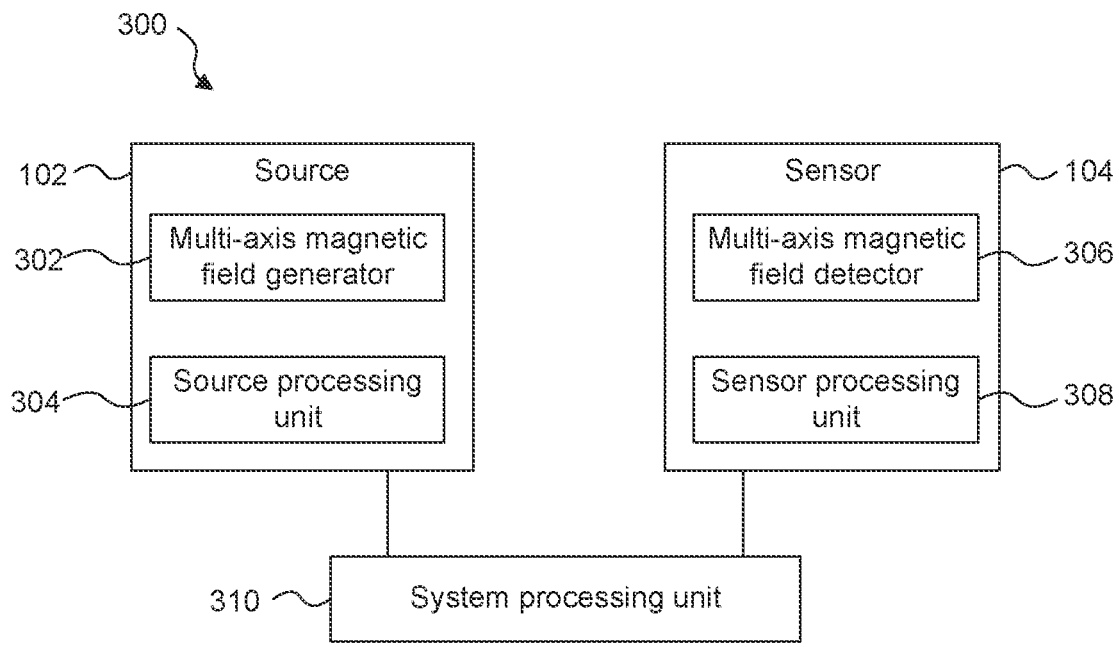
FIG. 3 shows parts of a magnetic positioning system.

The accompanying drawings illustrate various examples. The skilled person will appreciate that the illustrated element boundaries (e.g., boxes, groups of boxes, or other shapes) in the drawings represent one example of the boundaries. It may be that in some examples, one element may be designed as multiple elements or that multiple elements may be designed as one element. Common reference numerals are used throughout the figures, where appropriate, to indicate similar features.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art. Embodiments will now be described by way of example only.

The basic concepts of how a magnetic positioning system can be used to determine the relative positions and orientations of a multi-axis magnetic field source 102 and a multi-axis magnetic field sensor 104 are described in the background section above. However, in contrast to the systems described in the background section above, the magnetic positioning systems described below are configured for use in systems (e.g. surgical robotic systems) that require high precision in an environment which includes a lot of conducting material (e.g. metal). Neither of the two conventional approaches for implementing magnetic positioning systems described in the background section (the high frequency AC approach and the switched DC approach) are suitable for use in these systems. In particular, the magnetic positioning systems described below use low frequency signals (e.g. frequencies below 1 kHz) so that distortion caused by eddy currents is low, in a manner which provides a better signal to noise ratio than has previously been known in the switched DC approach, thereby leading to higher precision and/or faster measurement times compared to the conventional switched DC approach. To give some examples, the low frequency signals could have frequencies less than 100 Hz or less than 50 Hz, e.g. 10 Hz.

The methods described below relate to the same arrangement as shown in FIG. 1 which shows the position and orientation of a multi-axis magnetic field source 102 and a multi-axis magnetic field sensor 104. The source 102 may be implemented with perpendicular coils as shown in FIG. 2a. In this example, the source 102 is a 3-axis electromagnet source that can be excited on each of its axes by providing source signals as currents to the respective coils for the axes. The sensor 104 may be implemented with one or more magnetometer sensors (such as flux-gates, magnetoresistive sensors or AMR sensors) on its axes. In different embodiments, the sensor may be implemented as a 3-axis receiver coil, with three perpendicular coils, similar to the source 102.

FIG. 3 schematically shows a magnetic positioning system 300 which comprises the multi-axis magnetic field source 102 and the multi-axis magnetic field sensor 104. The source 102 comprises a multi-axis magnetic field generator 302 which is configured to generate a magnetic field, and which may be implemented as a plurality of perpendicular coils as shown in FIG. 2a. The source 102 also comprises a source processing unit 304 which is configured to provide source signals to excite the axes of the multi-axis magnetic field generator 302. Although FIG. 3 shows the source processing unit 304 as being part of the source 102, in other implementations, the source processing unit 304 may be physically located outside of the source 102 and connected to the source 102 so that it can provide the source signals to excite the axes of the multi-axis magnetic field generator 302. The sensor 104 comprises a multi-axis magnetic field detector 306 which is configured to detect a magnetic field, and which may be implemented as one or more non-coil based, DC-sensitive magnetometers that can detect the magnetic field along a plurality of axes as shown in FIG. 2b or as a plurality of perpendicular coils. Using a single magnetometer with a plurality of axes allows the magnetic field strength to be detected in all axes at the same physical point in space. Using a plurality of magnetometers to measure the magnetic field, in slightly different locations, along the respective plurality of axes is an option but may be slightly more complex than using a single magnetometer. For example, fluxgate magnetometers, anisotropic magnetoresistive (AMR) and tunnelling magnetoresistive (TMR) sensors, or other magnetic sensors could be used in the multi-axis magnetic detector 306. The sensor 104 also comprises a sensor processing unit 308 which is configured to analyse the detected magnetic field. Although FIG. 3 shows the sensor processing unit 308 as being part of the sensor 104, in other implementations, the sensor processing unit 308 may be physically located outside of the sensor 104 and connected to the sensor 104 so that it can receive signals from the multi-axis magnetic field detector 306. The magnetic positioning system 300 also comprises a system processing unit 310 which can be used to combine information from the source 102 and the sensor 104 in order to determine the relative positions and/or orientations of the source 102 and the sensor 104.

Figure 4:
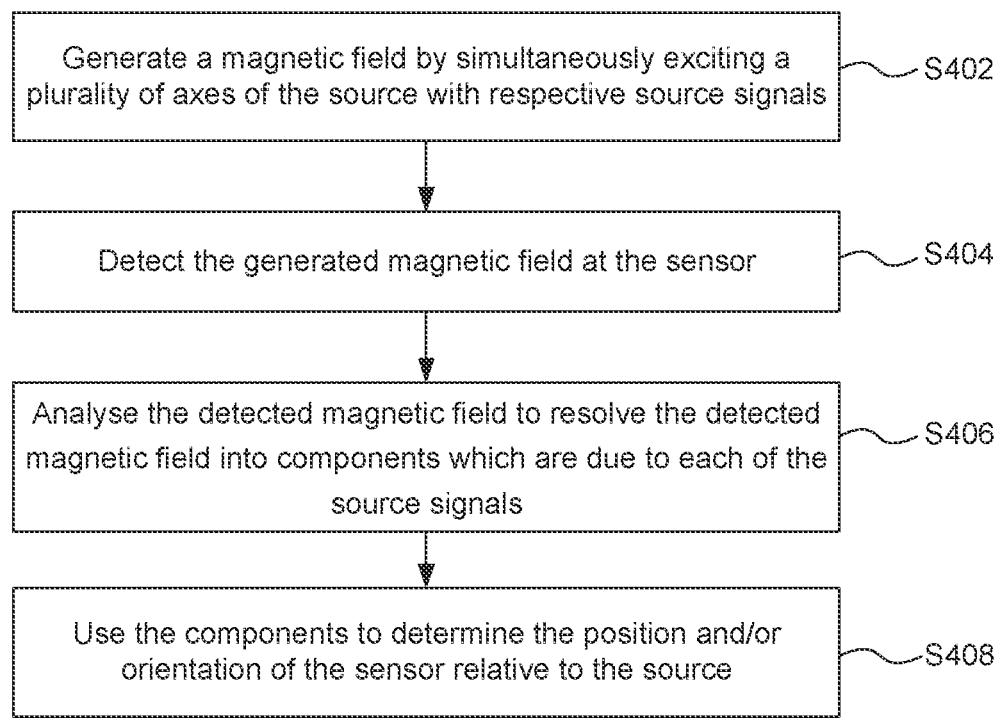
FIG. 4 is a flow chart for a magnetic positioning method.

FIG. 4 is a flow chart for a magnetic positioning method which can be implemented by the magnetic positioning system 300. In step S402 the multi-axis magnetic field source 102 generates a magnetic field by simultaneously exciting a plurality of axes of the multi-axis magnetic field source 102 (e.g. of the multi-axis magnetic field generator 302) with respective source signals that are orthogonal to each other over a time period, T. In this way, the source 102 can produce three excitation vectors that are linearly independent. To give an example, the period T may be in a range from 10 ms to 10 s, but in some other implementations the period T could be outside of this example range. The source processing unit 304 may control the excitation of the axes of the multi-axis magnetic field generator 302 with the source signals. The generated magnetic field is a superposition of the magnetic fields generated from the plurality of axes. It is mathematically easier to analyse and think of the magnetic field as a number of superposed magnetic fields, because the maths for each constituent magnetic field is relatively easy. The generated magnetic field is a spatially-unique, time-dependent field.

Mathematical functions can be described as being "orthogonal" to each other over a period, T, when the integral of the product of the functions over the period, T, is zero. More precisely, in mathematics, orthogonal functions belong to a function space that is a vector space equipped with a bilinear form. When the function space has an interval as the domain, the bilinear form may be the integral of the product of functions over the interval:

$$\langle f,g \rangle = \int_a^b f(x)g(x)dx,$$

where the interval given by the limits a and b is equal to the period, T. The functions f and g are orthogonal when this integral is zero, i.e. $\langle f,g \rangle = 0$ whenever $f \neq g$. For example, if the source signals are sine-waves with different integer numbers of cycles in the period, T, then they are orthogonal to each other over the period, T. The "orthogonality" of the source signals is independent of the physical axes which they excite, i.e. the orthogonality of the source signals does not relate to the spatial orientation of the axes of the source 102, e.g. whether the axes are perpendicular to each other or not.

In step S404, the multi-axis magnetic field sensor 104 detects the magnetic field generated by the source 102, e.g. using the multi-axis magnetic field detector 306. The multi-axis magnetic field sensor 104 detects the magnetic field along multiple axes (e.g. three axes). As shown in FIG. 2b, the sensor 104 may comprise one or more magnetometers configured to detect the magnetic field along three perpendicular axes. The multi-axis magnetic field sensor 104 determines, for each of its axes, an axis-specific sensor signal representing the detected magnetic field for that axis. Each of the axis-specific sensor signals includes components from all three source signals. For example, if the source axes are denoted (x,y,z) and the sensor axes are denoted (a,b,c) then each of the axis-specific sensor signals ($R_a$ for axis a, $R_b$ for axis b and $R_c$ for axis c, which may collectively be described with a vector $R=[R_a, R_b, R_c]^T$) comprises components originating from the three source axes (x,y,z) (wherein the source signals may be denoted $T_x$ for axis x, $T_y$ for axis y and $T_z$ for axis z, which may collectively be described with a vector $T=[T_x, T_y, T_z]^T$). A 3×3 matrix, S, can be used to represent the detected magnetic field at the sensor, such that R=ST, wherein the matrix has the form:

$$S = \begin{bmatrix} S_{xa} & S_{ya} & S_{za} \\ S_{xb} & S_{yb} & S_{zb} \\ S_{xc} & S_{yc} & S_{zc} \end{bmatrix}.$$

Where we describe analysing the detected magnetic field herein, it is to be understood that this can be done by analysing the axis-specific sensor signals representing the detected magnetic field for the axes of the sensor 104.

In step S406, the detected magnetic field is analysed over an analysis interval which is at least as long as the period, T, to resolve the detected magnetic field into components which are due to each of the plurality of source signals. For example, the axis-specific sensor signals are resolved into components which are due to the source signals. Each "component" is due to a single one of the source signals. It is possible to split up the detected magnetic field (e.g. the sensor signals) into components due to the source signals because the source signals are orthogonal. Since the source signals are orthogonal, the components of the detected magnetic field can be described as "separable" or "independent". Resolving the detected magnetic field (e.g. the sensor signals) into components is similar to resolving a vector into components along orthogonal directions. Step S406 involves "determining" or "identifying" the components of the detected magnetic field which are due to each of the plurality of source signals. For example, in the case of a low-frequency AC system as described herein, the received signal on each axis-sensor can be considered to be the sum of some fraction of $T_x$, some fraction of $T_y$, and some fraction of $T_z$, which are sinewaves at different frequencies and which are orthogonal over the period, T. The values of the fractions that are referred to above as "some fraction of $T_x$", "some fraction of $T_y$", and "some fraction of $T_z$" are given by the values in the matrix, S, that are relevant for the sensor signal in question (e.g. $S_{xa}$, $S_{ya}$ and $S_{za}$ for the first sensor signal $R_a$; $S_{xb}$, $S_{yb}$ and $S_{zb}$ for the second sensor signal $R_b$; and $S_{xc}$, $S_{yc}$ and $S_{zc}$ for the third sensor signal $R_c$). Since the source signals ($T_x$, $T_y$ and $T_z$) are orthogonal, the composite received sensor signals can be resolved to determine the signs and magnitudes of the different frequency components, e.g. using a Fourier transform, or Fourier integrals. In the case of a switched-DC method, the change in each received axis-sensor signal when first the $T_x$ source is switched (then when the $T_y$ source is switched, and then when the $T_z$ source is switched) can be analysed.

With reference to the example of the matrix given above, a first axis-specific sensor signal $R_a = S_{xa}T_x + S_{ya}T_y + S_{za}T_z$ and this first axis-specific sensor signal can be considered to include three "components" ($S_{xa}T_x$, $S_{ya}T_y$ and $S_{za}T_z$) which are each due to a different one of the source signals ($T_x$, $T_y$ and $T_z$). Similarly, a second axis-specific sensor signal $R_b = S_{xb}T_x + S_{yb}T_y + S_{zb}T_z$ and this second axis-specific sensor signal can be considered to include three "components" ($S_{xb}T_x$, $S_{yb}T_y$ and $S_{zb}T_z$) which are each due to a different one of the source signals ($T_x$, $T_y$ and $T_z$). Similarly, a third axis-specific sensor signal $R_c = S_{xc}T_x + S_{yc}T_y + S_{zc}T_z$ and this third axis-specific sensor signal can be considered to include three "components" ($S_{xc}T_x$, $S_{yc}T_y$ and $S_{zc}T_z$) which are each due to a different one of the source signals ($T_x$, $T_y$ and $T_z$). The analysis of the detected magnetic field performed in step S406 may be performed by the multi-axis magnetic field sensor 104 (e.g. the sensor processing unit 308) or by the system processing unit 310. As an example, in step S406, the magnetic positioning system analyses the detected magnetic field by processing the axis-specific sensor signals over the analysis interval to resolve the detected magnetic field into components which are due to the plurality of source signals. The analysis interval may be equal to the period, T. In other examples, the analysis interval may be longer than the period, T. In some examples, the analysis interval may be a multiple of the period, T, e.g. the analysis interval may be equal to 2 T. The analysis performed in step S406 may involve a Fourier analysis of the axis-specific sensor signals over the analysis interval. In particular, the magnetic positioning system may implement a Fast Fourier Transform (FFT) or discrete Fourier integrals to analyse the detected magnetic field over the analysis interval to resolve the detected magnetic field into components which are due to the plurality of source signals.

In step S408, the magnetic positioning system (e.g. the system processing unit 310 or the sensor processing unit 308) uses the components to determine one or both of the position and the orientation of the multi-axis magnetic field sensor 104 relative to the multi-axis magnetic field source 102. Where the magnetic positioning system determines both the relative positions and orientations of the source 102 and the sensor 104 in 3D space, this involves determining six parameters for the six degrees of freedom (three for the relative positions and three for the relative orientations). In other situations the magnetic positioning system may determine only the relative positions or only the relative orientations of the source 102 and the sensor 104. As mentioned in the background section above with reference to FIG. 1, a person skilled in the art would know how to use the components determined by resolving the detected magnetic field to determine one or both of the position and the orientation of the multi-axis magnetic field sensor 104 relative to the multi-axis magnetic field source 102, so the details of this process are not described in detail here. In the example shown in FIG. 3 there is a system processing unit 310 which can communicate with both the source 102 and the sensor 104 (e.g. via wired or wireless communication links), but in some other examples, the magnetic positioning system might not include a system processing unit, in which case the sensor processing unit can perform all of the necessary processing to determine the relative positions and/or orientations of the source 102 and the sensor 104.

The source 102 may be configured to continually excite all of its axes over a plurality of the periods, and the sensor 104 may be configured to repeatedly resolve the detected magnetic field to thereby continuously track the relative positions and/or orientations of the source 102 and the sensor 104. However, in other examples, separate, discrete determinations of the relative positions and/or orientations of the source 102 and the sensor 104 may be made rather than continuously tracking.

The source signals are "low frequency" signals, e.g. they have frequencies below 1 kHz. For example, each of the source signals may have a frequency in a range from 1 Hz to 500 Hz. By using low frequencies such as this, eddy currents that may be generated in electrically conducting material in the vicinity will not introduce much distortion into the magnetic field. The frequencies that are used may depend on the application, the required measurement-time or update-rate, and the required immunity to metal. A narrow range of frequencies may be used in a particular implementation such that the ratio between the highest frequency and the lowest frequency used for the source signals is not more than 3:1 or not more than 2:1 to give two examples.

Each of the source signals may have a frequency such that it has a number of cycles, x, in the period, T, wherein 1≤x≤50. As a more specific example, 3≤x≤25. This is a small number of cycles compared to in the high frequency AC methods described in the background section above which would often have hundreds or thousands of cycles in a measurement period (or "analysis interval"). In the method described herein with reference to FIG. 4, we can use such low numbers for x because the different source signals are orthogonal to each other over the period, T, so if we analyse the signals over an analysis interval which is at least as long as the period, T (in particular when the analysis interval equals T or a multiple of T), then the cross-interference between the different source signals is very low (e.g. theoretically zero). This means that sufficient SNRs can be obtained even when having such low numbers of cycles, x, in the period, T. In turn this means that the precision of the magnetic positioning system can be increased and/or the analysis interval can be shortened compared to the conventional approaches described in the background section above.

So in the methods described herein with reference to FIG. 4, the axes of the source 102 are simultaneously excited with source signals at low frequencies to generate a magnetic field, and the sensor 104 is able to detect the generated magnetic field, and resolve the detected magnetic field into components due to the source signals without mutual interference. The source signals may be sinusoidal. Using sinusoidal source signals (e.g. rather than square-wave signals) reduces the high frequency components in the magnetic field.

Figure 5A:
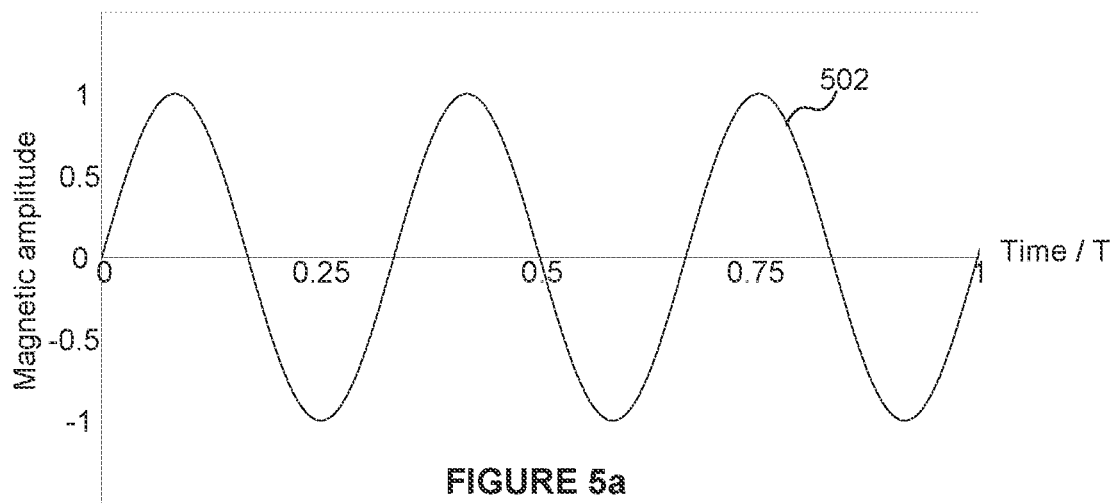
FIG. 5a is a graph illustrating the magnetic amplitude associated with a first source signal as a function of time.
Figure 5B:
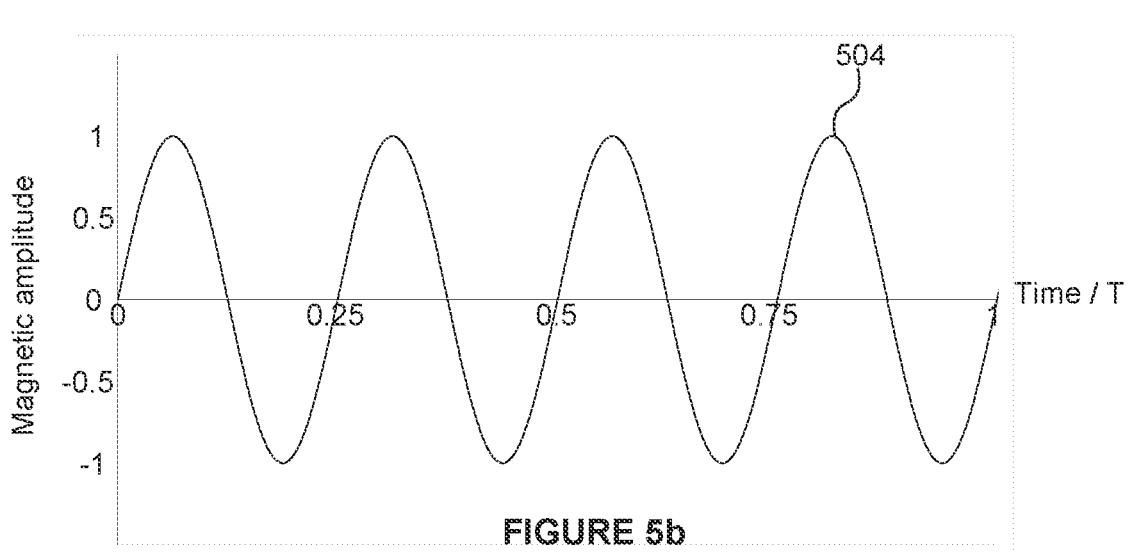
FIG. 5b is a graph illustrating the magnetic amplitude associated with a second source signal as a function of time.
Figure 5C:
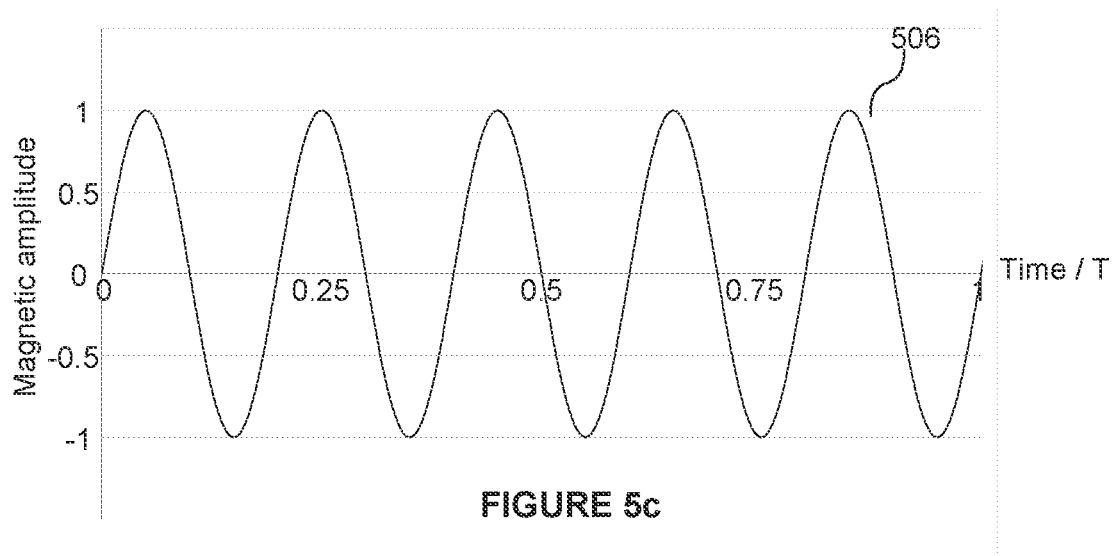
FIG. 5c is a graph illustrating the magnetic amplitude associated with a third source signal as a function of time.

FIGS. 5a, 5b and 5c show graphs illustrating the magnetic amplitudes associated respectively with a first source signal 502, a second source signal 504 and a third source signal 506 as a function of time over the period, T (which may be referred to as a "fundamental period"). The value of T could take any suitable value, e.g. T could be in a range from 50 ms to 5 s, and to give a specific example T could be 1 second. In different scenarios different values of T may be suitable. The first, second and third source signals are used to excite the respective three axes of the source 102. The three source signals have different frequencies. It can be seen in FIGS. 5a to 5c that each of the source signals (502, 504 and 506) has a frequency such that it has an integer number of cycles in the period, T. In particular, the first source signal 502 has exactly 3 cycles in the period, T; the second source signal 504 has exactly 4 cycles in the period, T; and the third source signal 506 has exactly 5 cycles in the period, T. Although the source signals have different frequencies, their frequencies are of similar orders of magnitude. In the example shown in FIGS. 5*a* to 5*c*, each frequency undergoes one more complete cycle in the period, T, than the previous frequency. In this example, the frequencies of the source signals are not multiples of one another. Distortions (e.g. non-linearities, etc.) in the electromagnet source or the sensor, may introduce some level of "harmonic distortion" (i.e. additional frequency components at multiples of the fundamental harmonic) so choosing the frequencies of the source signals so that they are not multiples of one another can help to reduce cross-interference between the signals. Since the source signals have different frequencies and each of the source signals has a frequency such that it has an exact integer number of cycles in the period, T, the source signals 502, 504 and 506 are orthogonal to each other over the period, T. The fundamental period, T, is of the order of the "update interval" for which a complete 3-axis measurement of the relative positions and/or orientations is to be determined.

A property of Fourier integrals is that the amplitude of each frequency component can be determined from a composite signal, without error or interference between the signals, if it is analysed over the fundamental period T. This means that we can excite all three axes of the source 102 simultaneously on a set of close, non-self-interfering frequencies—and deduce the exact magnitude of each component at the sensor 104. Furthermore, the measurement bandwidth (for noise) for each signal is of the order of 1/T Hz. When the processing is performed using a Fast Fourier Transform (FFT), the number of samples within the analysis interval should be a power of 2. For a 3-axis system another way of decoding the signals is to use a set of three discrete Fourier integrals, which would be more computationally efficient. The sampling rate at the sensor 104 typically needs to be at least four times the highest frequency transmitted, to ensure the amplitude and phase of the highest frequency can be determined. To avoid aliasing, the sampling rate can be set to be higher than this minimum sampling rate.

The magnetic positioning system may be configured to resolve the detected magnetic field into components which are due to each of the plurality of source signals once per update interval, and use the components to determine one or both of the position and the orientation of the multi-axis magnetic field sensor relative to the multi-axis magnetic field source once per update interval, wherein the update interval is equal to or shorter than the analysis interval. In particular, the update interval may be less than or equal to the period T.

In a system engineered such that the period, T, and the 'update interval' is comparable to the update interval of a conventional switched DC system (in which the update interval is the cumulative time to make the three-axis measurements sequentially), advantages of the methods described herein with reference to FIG. 4 include:

- there can be lower measurement noise, as the individual measurement time for each axis is longer, and the noise can be near to ideally band-limited;
- using sinewaves rather than square-waves as the source signals means there is less high-frequency content, which:
    - inherently means there is a deeper skin-depth and less spatial distortion caused by any electrically conducting material (e.g. metal) in the vicinity, even before applying more sophisticated processing;
    - is better for staying below human exposure field strength limits set by the International Commission on Non-Ionizing Radiation Protection (ICNIRP), wherein the limits are lower at higher frequencies;
    - is less likely to generate audible clicks or buzzing; and
    - results in the effective measurement bandwidth (hence noise) being narrowed as it does not need to include the square-wave higher-frequency harmonics;
- all three axes are monitored continually in time, so if the relative position of the source and sensor moves during the measurement, the effects will be relatively similarly averaged in all axis measurements; and
- impulsive interference will have less severe effects than in switched DC systems.

It is noted that the magnetic positioning system is not configured for transmitting data from the source 102 to the sensor 104. The source 102 generates substantially the same magnetic field every period, T, and the sensor 104 detects the generated field and analyses it. The sensor 104 analyses how the amplitudes and polarities (and optionally the phases) change for the axis-specific sensor signals to determine the relative positions and/or orientations of the source 102 and the sensor 104.

If the (absolute) position and orientation of the source 102 are known then the magnetic positioning system can be used to determine the (absolute) position and/or orientation of the sensor 104. Similarly, if the (absolute) position and orientation of the sensor 104 are known then the magnetic positioning system can be used to determine the (absolute) position and/or orientation of the source 102.

If Fourier integrals are performed over an analysis interval equal to the fundamental period T, interference may occur due to "end effects" in the analysis interval. This could be caused by periodic interference sources which are not harmonic in the period T, or changes in magnetic field which vary very slowly, with a period (if periodic at all) much larger than T. These end effects may reduce the precision in the position and orientation measurements determined by the magnetic positioning system.

The problems caused by the end effects may be overcome by performing the analysis on data which has been 'windowed'. This means that the magnetic positioning system (e.g. the sensor processing unit 308 or the system processing unit 310) processes the axis-specific sensor signals (i.e. the signals from each receiver axis) by multiplying them by a window function to determine windowed axis-specific sensor signals, and then processes the windowed axis-specific sensor signals over the analysis interval to resolve the detected magnetic field into components which are due to each of the plurality of source signals. The window function may be a sinusoidal window function. In particular, the window function may be a raised cosine window function, which may be referred to as a "Hann window".

Using the window function filters the time-domain sensor signals to provide signals with more limited frequencies. In other words, high frequency components (e.g. representing step changes in the time domain) in the sensor signals are removed (or at least significantly reduced) by the window function. Using the window function reduces the energy of components in the sensor signals that are not periodic and could end up spilling into adjacent frequency bins and causing intersignal interference. Using the window function also helps to reduce "spectral splatter", which may be caused by an abrupt change in received signal due to some interference.

Figure 6:
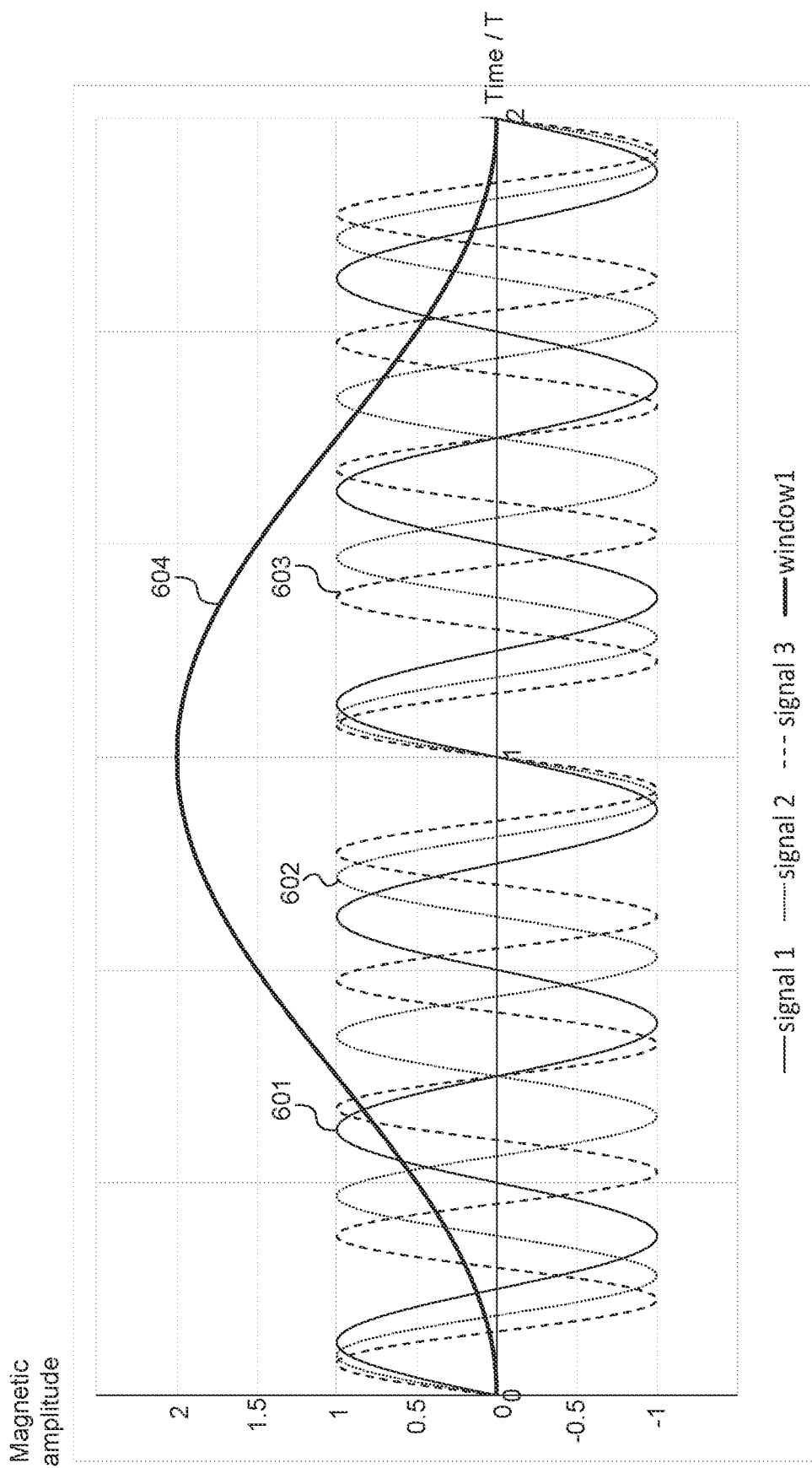
FIG. 6 is a graph illustrating the magnetic amplitudes associated with the first, second and third source signals as well as a window function over time.

FIG. 6 is a graph illustrating the magnetic amplitudes associated with the first source signal 601, the second source signal 602 and the third source signal 603 (shown in FIGS. 5*a* to 5*c*) as well as a window function 604 over time. The graph in FIG. 6 has time along the horizontal axis from 0 to 2 T. The window function 604 is a sinusoidal window function. In particular, the window function 604 is a raised cosine function with a period of 2 T. In this case, the analysis interval over which the windowed axis-specific sensor signals are processed is 2 T. That is, the analysis interval is equal to the period of the window function. Using a raised cosine window function with a period of 2 T retains orthogonality of the source signals when analysed over the period of the window function. Higher multiples of T can be used as the period of the window function, but this may be less preferred because it would increase the analysis interval and hence reduce the rate at which the magnetic positioning system can determine the relative positions and/or orientations of the source 102 and the sensor 104.

The sensor signals are multiplied by the window function before Fourier analysis, in which the windowed signals are analysed over an analysis interval of 2 T. Since the window function 604 is sinusoidal and has a period of 2 T, it has the property that when added to itself with a time-offset of T, its amplitude sums to a constant. This ensures all time-intervals within the repeat-interval T are equally-weighted, thereby preserving the orthogonality in the source signals.

Figure 7A:
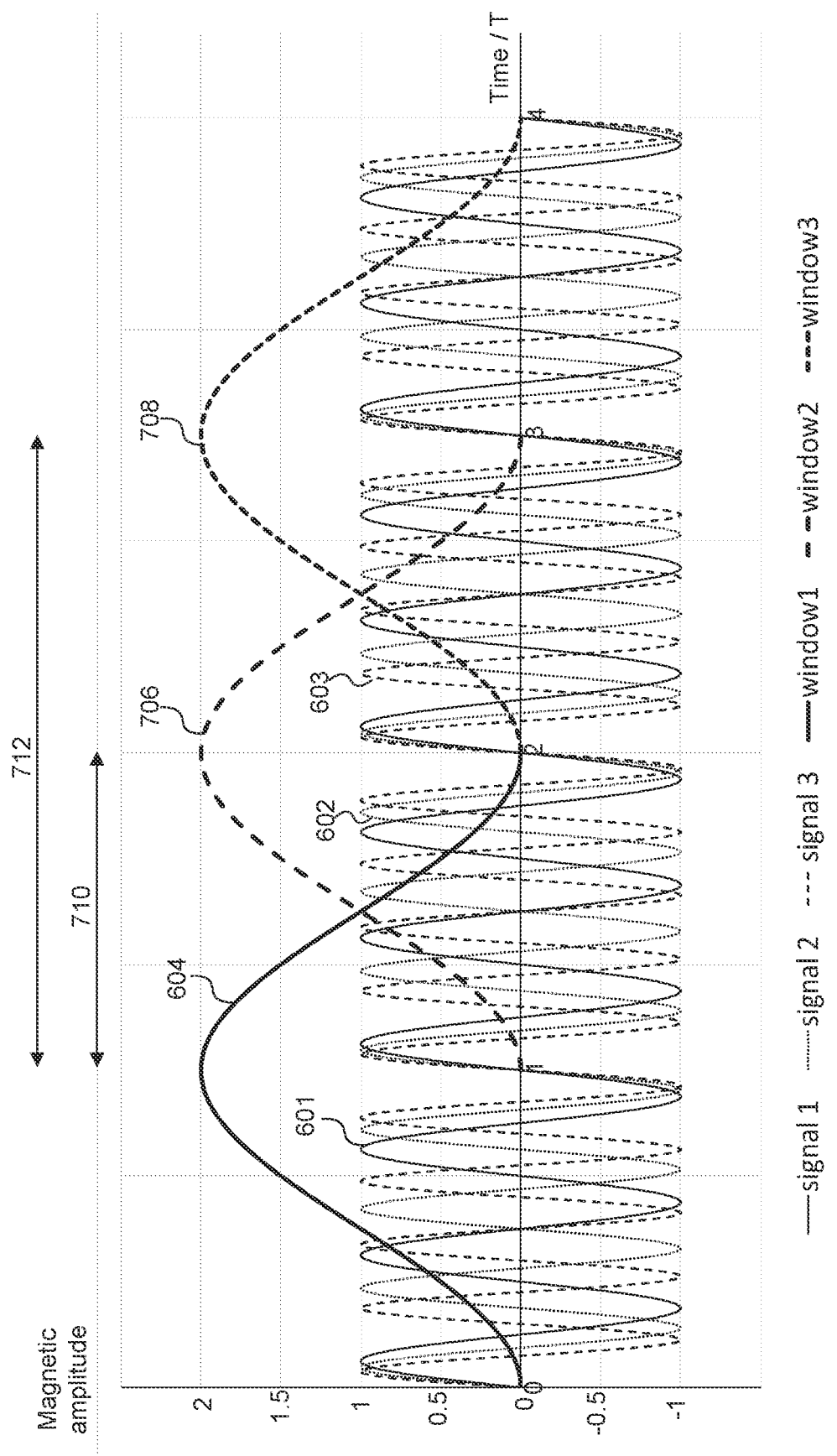
FIG. 7a is a graph illustrating the magnetic amplitudes associated with the first, second and third source signals as well as first, second and third window functions over time.

Although the analysis interval is 2 T when the window function 604 is used, the magnetic positioning system may determine the relative positions and orientations of the source and the sensor 104 once per update interval, and it may be beneficial for the update interval to be shorter than the analysis interval. A respective window may be used for each update interval, such that the window functions may be overlapping in time. An example of this is shown in FIG. 7*a*, which is a graph illustrating the magnetic amplitudes associated with the first source signal 601, the second source signal 602 and the third source signal 603 (shown in FIGS. 5*a* to 5*c*) as well as the first window function 604 (shown in FIG. 6), a second window function 706 and a third window function 708 over time. The graph in FIG. 7*a* has time along the horizontal axis from 0 to 4T. The second and third window functions (706 and 708) match the first window function 604 in that they are raised cosine functions with periods of 2 T. In this example, the second window function 706 is shifted in time relative to the first window function 604 by T (i.e. by half of the period of the window functions), and the third window function 708 is shifted in time relative to the second window function 706 by T. So in this example there is a succession of 50%-overlapping windows wherein measurements are taken at time intervals T, using windowed data from the past 2 T. Using overlapping window functions like this can be particularly useful for a system designed to capture motion because it allows the update interval to be shorter than the analysis interval. Overlapping windows are used where the system analyses a continuous signal in short intervals of time. The window functions are used to band-limit interference from external sources which in general is not periodic in T. Furthermore, the window functions should maintain the orthogonality of the signals so that they do not interfere with one another. The 50% overlapping window functions shown in FIG. 7*a* remove this interference and splatter by analysing the signal at time intervals T using windowed data of the past 2 T without having to wait for 2 T between updates, so giving the system a faster update rate. FIG. 7*a* indicates an update interval 710 (which has a duration of T in this example) and an analysis interval 712 (which has a duration of 2 T in this example).

Figure 7B:
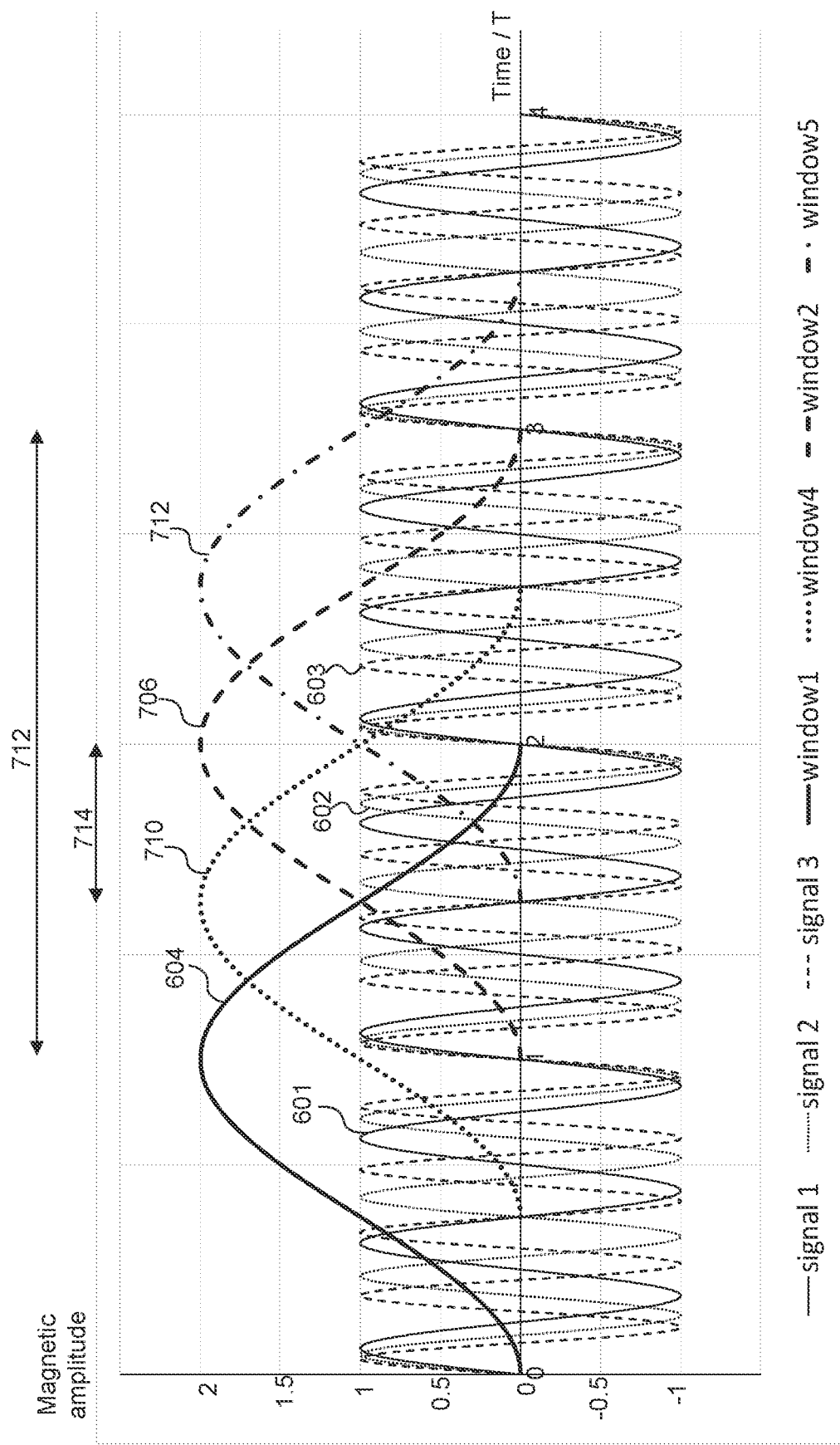
FIG. 7b is a graph illustrating the magnetic amplitudes associated with the first, second and third source signals as well as first, second, fourth and fifth window functions over time.

The window functions could be more overlapping (i.e. overlapping by more than 50%), such that the data is sampled more frequently, e.g. the update interval could be T/2, or indeed at any arbitrary time interval (typically less than or equal to T). An example of window functions which overlap by more than 50% is shown in FIG. 7*b*, which is a graph illustrating the magnetic amplitudes associated with the first source signal 601, the second source signal 602 and the third source signal 603 (shown in FIGS. 5*a* to 5*c*) as well as the first window function 604 (shown in FIGS. 6 and 7*a*), the second window function 706 (shown in FIG. 7*a*), a fourth window function 710 and a fifth window function 712 over time. The graph in FIG. 7*b* has time along the horizontal axis from 0 to 4T. The fourth and fifth window functions (710 and 712) match the first and second window functions 604 and 706 in that they are raised cosine functions with periods of 2 T. In this example, the fourth window function 710 is shifted in time relative to the first window function 604 by T/2 (i.e. by a quarter of the period of the window functions), the second window function 706 is shifted in time relative to the fourth window function 710 by T/2, and the fifth window function 712 is shifted in time relative to the second window function 706 by T/2. So in this example there is a succession of 75%-overlapping windows wherein measurements are determined at time intervals T/2, using windowed data from the past 2 T. FIG. 7*b* indicates an update interval 714 (which has a duration of T/2 in this example) and the analysis interval 712 (which has a duration of 2 T in this example).

A number of different time periods (or "intervals") are described herein:

The fundamental period, T, is the time for which f(t)=f(t+T) for all the excitation source signals, i.e. the period within which there are an integer number of cycles of all the emitted magnetic signals.

The analysis interval is the length of time over which the signals are analysed, and where a window function is used the analysis interval is the length of the window function (e.g. which may be a multiple of T, typically 2 T as shown in the example in FIG. 7*a*).

The update interval (for a motion-tracking application) is the interval between successive measurements or windows (e.g. the time-offset between windows 604, 706 and 708 in FIG. 7*b*). The update interval may be equal to T as shown in FIG. 7*a*. As another example, the update interval may be T/2 as shown in FIG. 7*b*. In other examples, the update interval may be decoupled from the fundamental period, T, i.e. it could be an arbitrary time, e.g. less than half the analysis interval.

From a purely signal-processing perspective having an update interval much less than T would result in redundant (over-sampled) information. However, in practice it allows the update rate used by the system to be somewhat decoupled from the fundamental period T. This could be a significant benefit in moving and interactive applications where it may be desirable to synchronise the update rate to an arbitrary video/display frame-rate. For example, this could help minimise latency and avoid motion-artifacts for systems where the application 'frame rate' might be (for example) 60 Hz but motion-system considerations dictate a slightly longer fundamental period, T, e.g. corresponding to 25-40 Hz.

In the examples given above the source signals are orthogonal to each other over the period, T, because they have different frequencies and each have an exact integer number of cycles in the period, T. There are other ways in which different source signals could be orthogonal to one another over the period, T. For example, two of the source signals may have phases which differ by $$\frac{\pi}{2},$$

such that those two source signals are orthogonal to each other over the period, T. For example, sine and cosine waves at the same frequency are orthogonal over a period which is a multiple of their period. Therefore, sine and cosine waves (which have phases that differ by $$\frac{\pi}{2})$$

could be used as separate source signals. This may add complexity in that a more-accurate timing relationship (and knowledge of any phase-delays in the electronics or signal-processing pipeline) may be needed between the source 102 and the sensor 104 to prevent crosstalk between the sine and cosine signals on the same frequency. Eddy currents in nearby metal which cause phase shifts could also cause variable crosstalk.

Explicit time synchronisation between the source 102 and the sensor 104 are not as important as in the conventional switched DC systems, however some time reference or other method may be used to be able to determine the sign (in-phase or anti-phase) of each sensor component, relative to the excitation. In this way, the magnetic positioning system may synchronise the timing of the multi-axis magnetic field source 102 and the multi-axis magnetic field sensor 104 with each other. There are various ways in which the timing of the source 102 and the sensor 104 could be synchronised with each other, as explained below:

An out-of-band time-reference signal may be provided to the multi-axis magnetic field source 102 and to the multi-axis magnetic field sensor 104. This could be done by having a single electronics module (e.g. the system processing unit 310) running both the source 102 and the sensor 104, or a wired link between separate source and sensor subsystems, or a separate radio link, or an infra-red link, or any other suitable link.

The multi-axis magnetic field source 102 may excite one or more of its axes with an additional time-reference signal which has a period of 2 T. For example, for systems with a single magnetic field source (or multiple sources synchronised by other means) a system of generating an additional component with a period of 2 T, separately analysed over a window of period of 4T, can be implemented. This can provide a phase-reference to the period, T, independent of its own received polarity.

The multi-axis magnetic field source 102 may simultaneously excite one of its axes with two source signals which have no common periodicity in intervals which are submultiples of the period, T. These two source signals may be used to derive a phase-reference in time (independent of received polarity).

Pilot tones may be used for synchronisation.

Magnetic signals used for time-synchronisation purposes need not necessarily be emitted from the same physical electromagnet or coil sources as those used more-directly for position-determination.

For stationary (or extremely slowly or only-occasionally moving) applications, the methods described herein with reference to FIG. 4 can be applied with very long analysis intervals of seconds, tens of seconds, or much longer still in order to obtain accurate position-measurements from very weak signals. Compared to the switched DC methods described in the background section above, the methods described herein with reference to FIG. 4 provide lower noise-bandwidth, and immunity to slowly-varying background fields, and therefore an ultimately better performance.

It may be considered preferable to use only sine waves (rather than cosine waves) for the source signals if making discrete position measurements (as opposed to time-continuous motion-measurements). This is because when using sine waves (in contrast to when using cosine waves), the generated magnetic field ramps up from zero at the start of the period T, and decays again to zero at the end of the period T (or 2 T), avoiding step-changes in the magnetic field at the start or end of the period.

Another way in which different source signals could be made to be orthogonal to one another over the period, T, is to use code modulation. Code modulation uses a cyclic code which exhibits a Kronecker delta self-correlation property; that is, when multiplied by itself: (i) when time-aligned, it correlates to itself, and (ii) at all other time-offsets (over the cycle period) it has zero, or very low and near-constant correlation. Example sequences that can be used for code modulation include de Bruijn sequences, including maximal-length pseudo-random bit sequences generated with appropriately-tapped linear feedback shift registers (LFSR). In these code modulation examples, the source signals are modulated with different orthogonal codes, such that the source signals are orthogonal to each other over the period, T. When code modulation is used, the different axes of the multi-axis magnetic field source 102 may generate the same code sequence over the period T, but with staggered offsets in time in some interval <T. In this way the detected signal from the different axes can be orthogonally recovered. Code modulation of this form spreads the frequency content of each channel (axis) over a wider bandwidth than sinusoidal schemes, and allows all channels to share a common frequency space, although the effective noise bandwidth can be comparable to sinusoid schemes. Whether this is a benefit or not may depend on the application in which the magnetic positioning system is being used, and on the character of any local potentially interfering magnetic noise sources. For example, whether the noise is narrowband single frequency drifting with time, or broadband etc.

The system can be extended to multiple sources within the same spatial vicinity, e.g. by using different excitation frequencies which remain orthogonal in the same common measurement period T. The additional sources could work collaboratively in the same system (e.g. to increase coverage, or measure relative positions of multiple objects with sources and sensors). For example, the magnetic positioning system may comprise a plurality of multi-axis magnetic field sources and a plurality of multi-axis magnetic field sensors, wherein each of the multi-axis magnetic field sources are configured to generate a magnetic field by simultaneously exciting a plurality of axes of the multi-axis magnetic field source with respective source signals, wherein all of the source signals for all of the multi-axis magnetic field sources are orthogonal to each other over the period, T. This approach can also be used to permit multiple independent magnetic positioning systems to function in the same space without causing interference between the different systems.

The different systems would not necessarily need to be explicitly time-synchronised as long as their clocks were sufficiently accurate that the period, T, in each system was substantially the same.

The examples described in detail herein relate to 3-axis magnetic field sources and 3-axis magnetic field sensors. In other words, the multi-axis magnetic field source 102 and the multi-axis magnetic field sensor 104 each have exactly three axes. In other examples, the sources and sensors could have a different number of axes, e.g. they could have 2 axes or 4 axes, or even more than 4 axes. In a system which just uses 2 axes, the system may be configured to determine 2D positions and orientations. The multiple axes of the source 102 may or may not be perpendicular and they may or may not all intersect at a point. Similarly, the multiple axes of the sensor 104 may or may not be perpendicular and they may or may not all intersect at a point.

When choosing the frequencies to use for the source signals (e.g. by the source processing unit 304), there may be advantages in keeping the range of frequencies (ratio of highest to lowest) limited, for example so that all channels are similarly affected by eddy-currents. In such a case it may be preferable to choose frequencies which have 7, 8 and 9 cycles within the period, T, rather than choosing frequencies which have 1, 2 and 3, or 3, 4 and 5 cycles within the period, T. It is noted that the examples shown in FIGS. 5a to 7b have frequencies which have 3, 4 and 5 cycles within the period, T for the purpose of improving the clarity of this disclosure.

In some examples, the multi-axis magnetic field source may be configured to simultaneously excite each of its axes with a plurality of source signals, wherein all of the source signals with which all of the axes are excited are orthogonal to each other over the period, T. Transmitting two or more frequencies simultaneously on each axis provides redundancy in case of interference on one frequency. Furthermore, if the multiple frequencies are at well-spaced frequencies, then their results can be analysed independently which may assist in estimation and further correction for eddy current distortions.

The frequencies may be chosen so as to operate in a band where the inherent receiver noise is lowest (e.g. 15-20 Hz may be preferable to 1-2 Hz even for very slow applications, if the sensor noise increases closer to DC), or to trade off sensor noise with skin depth. Furthermore, there may be reason to cycle frequencies periodically between axes and/or multiple sources in a system.

In some of the examples described above the source signals are sinusoidal signals at different frequencies with integer numbers of cycles in the period, T. However, in other examples, other waveforms may be used that also meet comparable orthogonality requirements in the period, T. These include (but are not limited to) square waves of different frequencies with integer numbers of cycles in the period, T. Rather than sinusoidal waves or square waves, the source signals could be 'softened' or partially-filtered square waves, or any other suitable waveform.

As an alternative to the windowing approach described above with reference to FIGS. 5a to 7b, a scheme which does not window the detected signals (e.g. by multiplying by a raised-cosine window function), and instead uses the de-facto 'rectangular window' (which is equivalent to using no window) prior to running the Fourier integrals could still achieve an acceptable end result, e.g. by analysing the detected magnetic field in a 'rolling' (i.e. overlapping) analysis period (of duration T) at time intervals which are some fraction of T, and low-pass filtering the results downstream.

FIG. 2a shows the source 102 as being a cube, but in other implementations it may be another shape, e.g. a tetragonal or flat PCB. The source 102 may have any suitable core, e.g. an air core, an iron core or a ferrite core to give just some examples. Electromagnet coil sources may be driven with well-defined current-waveforms. Rather than being a coil and acting as an electromagnet, in some implementations the multi-axis magnetic field source could comprise magnets (e.g. rare-earth/NdFeB magnets) which are physically spun by (well shielded) small motors at tightly controlled speeds and phases to generate the magnetic fields for the axes of the source at orthogonal frequencies. This could be a useful implementation when a very low-power source is needed.

Figure 8:
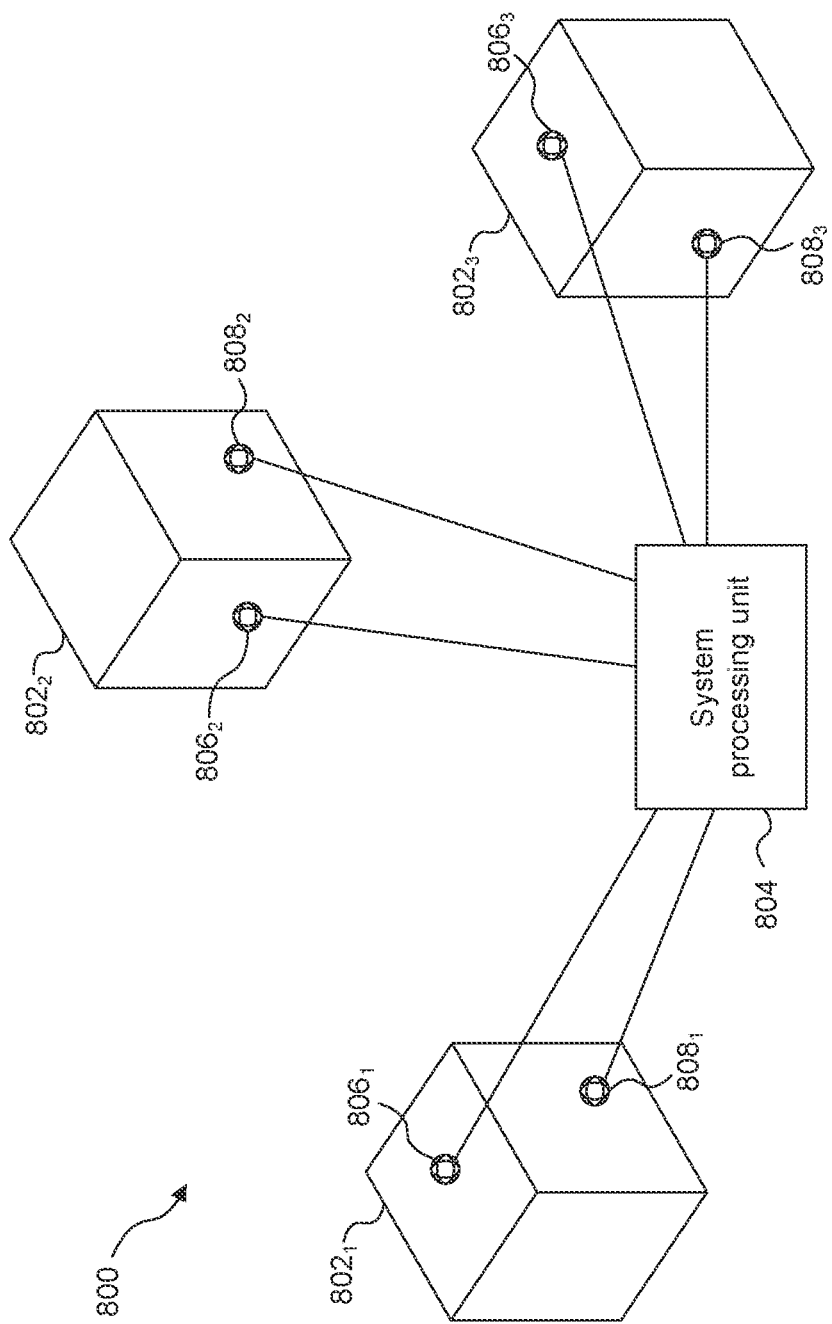
FIG. 8 shows a magnetic positioning system with multiple parts, each having a magnetic field source and a magnetic field sensor.

FIG. 8 shows a magnetic positioning system 800 with multiple parts (or "components"), each having a magnetic field source and a magnetic field sensor. In particular, the magnetic positioning system 800 comprises: (i) a first part $802_1$ with a first multi-axis magnetic field source $806_1$ and a first multi-axis magnetic field sensor $808_1$ secured to it, (ii) a second part $802_2$ with a second multi-axis magnetic field source $806_2$ and a second multi-axis magnetic field sensor $808_2$ secured to it, and (iii) a third part $802_3$ with a third multi-axis magnetic field source $806_3$ and a third multi-axis magnetic field sensor $808_3$ secured to it. The magnetic positioning system 800 also comprises a system processing unit 804 which can communicate with each of the sources 806 and each of the sensors 808 in the system via communication links which may be wired or wireless links. Each of the three sources 806 can be controlled to generate a respective magnetic field by simultaneously exciting its axes with source signals that are orthogonal over the period, T. If each of the three sources 806 has three axes then there are nine source signals in the system 800 which are all orthogonal with each other over the period, T. Each of the sensors 808 detect the generated magnetic fields, and the detected magnetic fields can be analysed (e.g. by the system processing unit 804) to determine the respective positions and orientations of the sources 806 and sensors 808 in the system 800.

Figure 9:
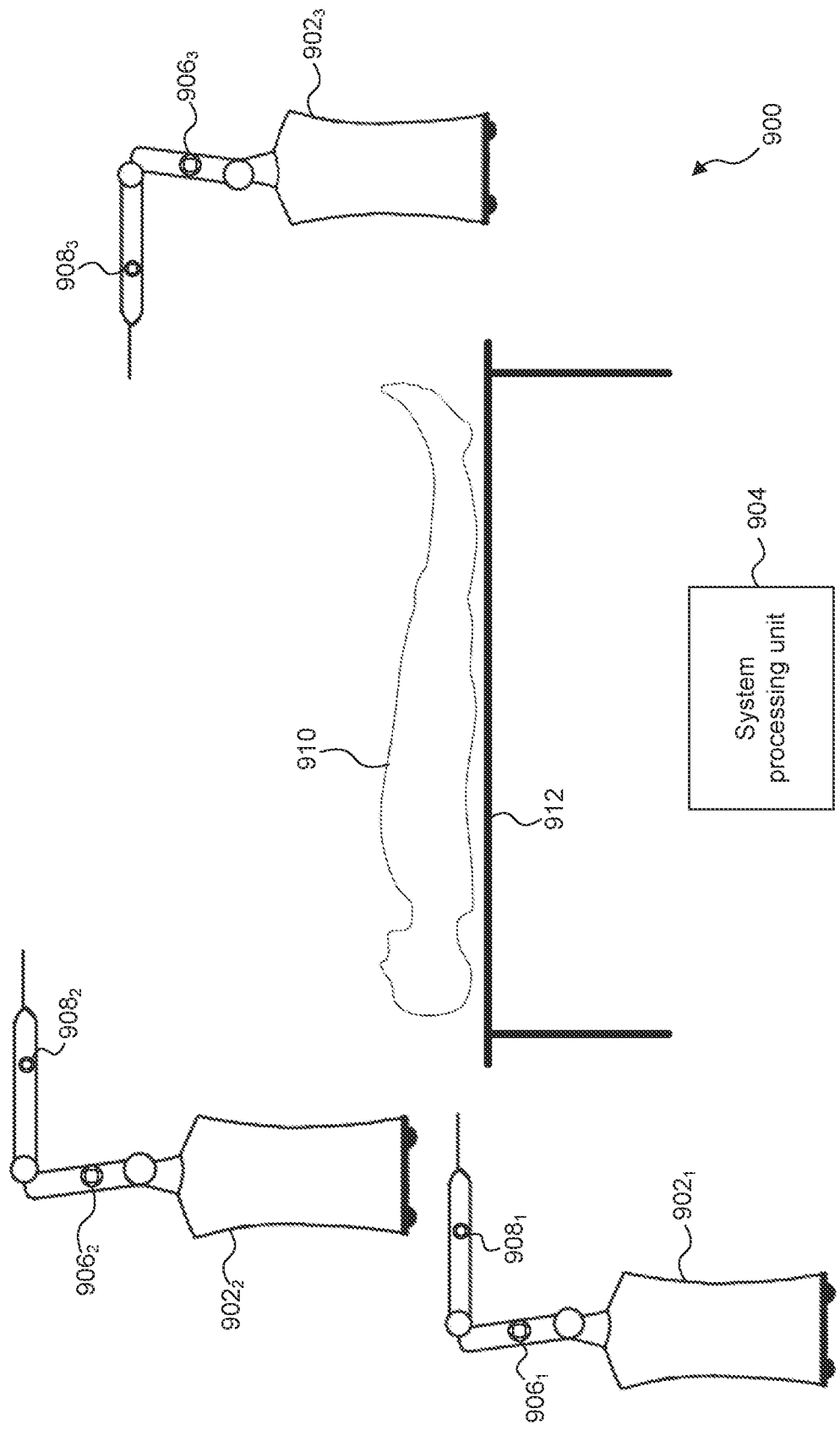
FIG. 9 shows a magnetic positioning system used in a surgical robotic system in an operating room.

FIG. 9 shows a magnetic positioning system used in a surgical robotic system 900 in an operating room. The surgical robotic system 900 comprises a plurality of parts (or "components") ($902_1$, $902_2$ and $902_3$) and a magnetic positioning system which comprises a plurality of multi-axis magnetic field sources ($906_1$, $906_2$ and $906_3$), a plurality of multi-axis magnetic field sensors ($908_1$, $908_2$ and $908_3$) and a system processing unit 904. The system processing unit 904 can communicate with each of the sources 906 and each of the sensors 908 in the surgical robotic system 900 via communication links which may be wired or wireless links. The parts 902 are surgical robot arms and/or carts supporting surgical robot arms. A respective one of the multi-axis magnetic field sources 906 and a respective one of the multi-axis magnetic field sensors 908 is secured to each of the parts 902. Also in the operating room is a patient 910 lying on an operating table 912.

More generally, the surgical robotic system 900 may comprise multiple parts (e.g. 5 carts supporting surgical robot arms), each with: (i) one or more multi-axis magnetic field sources 906 (all operating on different sets of frequencies), and (ii) one or more multi-axis magnetic field sensors 908. The sources and sensors may be directly mounted on a cart base or on a robot arm at known positions. Each of the parts 902 of the surgical robotic system 900 can use the magnetic positioning system to determine its relative positions and orientations to all of the other parts in the surgical robotic system, and then an optimal fit can be found to refine the determined positions and orientations, e.g. based on the relative accuracies and precision of the different measurements. As measurements of distance are typically more precise than bearing or orientation, the optimal fitting process may give more weighting to positions estimated using an element of trilateration. The magnetic positioning system (e.g. the system processing unit 904) is configured to analyse, for each of the parts 902, the magnetic field detected at the multi-axis magnetic field sensor 908 secured to that part to determine measurement information indicating one or both of the position and the orientation of that multi-axis magnetic field sensor 908 relative to the multi-axis magnetic field sources 906 secured to a plurality of the other parts 902. The magnetic positioning system (e.g. the system processing unit 904) is further configured to determine the positions and/or orientations of the parts 902 in the robotic surgical system using: (i) pre-determined information indicating, for each of the parts 902, the positions and orientations on that part at which the multi-axis magnetic field source 906 and the multi-axis magnetic field sensor 908 are secured, and (ii) the determined measurement information for each of the parts.

The magnetic positioning system may also use known geometrical arrangements of the parts 902 of the robotic surgical system to determine the positions and/or orientations of the parts 902 in the robotic surgical system. For example, knowing the joint angles and pose of the robot arms, the relative position of cart-bases can be determined by using appropriate coordinate transforms.

The use of multiple orthogonal source signals as described herein, permits all the measurements between all parts 902 to be made simultaneously in time. When constrained by a finite total measurement time (e.g. that may be <10 seconds to give an example), this allows the measurement- (and hence noise-) bandwidth for each constituent measurement to be much lower than would be the case for conventional switched-DC measurements which would have to be performed time-sequentially.

A system of optimally "refining" the estimates of relative cart positions may be used which takes account of the actual/relative precision (e.g. based on random or noise-related errors) of all the different constituent measurements either from applying a theoretical estimation of the error in different directions for a given measurement, or using statistical methods which consider the distribution of calculated positions and orientations obtained from a number of sub-measurements of each measurement.

Multiple sources and/or sensors may be implemented on each part to give more measurements, which may improve the accuracy of the determined positions and orientations. Angles may be inferred from position measurements to multiple points with known geometrical arrangements, as well as from direct angle measures.

For each of the parts 902, the respective multi-axis magnetic field source 906 and the respective multi-axis magnetic field sensor 908 are secured to the part at separated positions. For example, as shown in FIG. 9, the sources 906 are secured near the proximal end of the respective robot arms, and the sensors 908 are secured near the distal end of the respective robot arms). In this way the distance between the source and the sensor on a particular robot arm is relatively large (compared to the size of the robot arm itself). Physically separating the source and sensor on any one robot arm, helps to reduce the likelihood of the generated magnetic field from the source 906 on that robot arm 'overloading' the sensor 908 on that same robot arm.

In other examples, either the sources or the sensors (or both) could be secured to the cart (or even to a patient bed or other equipment in the OR) rather than the robot arm. However, having the sensors and/or sources further "up" the robot arm (i.e. further towards the distal end of the robot arm) may: (i) reduce the distance between a source on one robot arm and a sensor on another robot arm (which thereby reduces the noise and improves the precision of the position and orientation estimates), and (ii) keep a "direct path" between source and sensor further away from the patient bed 912 and other potential sources of distortion (e.g. other electrically conducting material in the operating room).

In another example, the sources and the sensors could be positioned in such a way that we know they are all within the same plane. For example, the sources and the sensors could be located in the cart in non-movable places, e.g. in the bottom of the cart. If all the sources and sensors are placed on the same plane (e.g. if they are all located at the same height), then the sources and sensors could be implemented as 2D sources and sensors, e.g. just having 2 axes in the common plane. In this example, 2D measurements would be used which would simplify the system compared to using 3D measurements.

In some examples, to manage the overall sensor dynamic range, there may be merit in not "listening" on the same part that is generating the magnetic field (e.g. if the sensor is physically close to the source on that part). This is because each part would have a sensor and a source and therefore the sensor on the part would be picking up the strongest signal from its own source. Optimal arrangements (for most precise signals in minimum measurement times) may involve generating magnetic fields on subsets of parts in succession. One drawback of this approach is that it would increase the overall measurement time.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A magnetic positioning system configured for use with a robotic surgical system, the magnetic positioning system comprising:
   a multi-axis magnetic field source configured to generate a magnetic field by simultaneously exciting a plurality of axes of the multi-axis magnetic field source with respective source signals that are orthogonal to each other over a period, T; and
   a multi-axis magnetic field sensor configured to detect the generated magnetic field by determining, for each of a plurality of axes of the multi-axis magnetic field sensor, an axis-specific sensor signal representing the detected magnetic field for that axis;
   wherein the magnetic positioning system is configured to:
      analyse the detected magnetic field by processing the axis-specific sensor signals over an analysis interval which is at least as long as the period, T, to resolve the axis-specific sensor signals into components which are due to the plurality of source signals; and
use the components to determine one or both of the position and the orientation of the multi-axis magnetic field sensor relative to the multi-axis magnetic field source,
wherein the magnetic positioning system is configured to process the axis-specific sensor signals by:
multiplying the axis-specific sensor signals by a window function to determine windowed axis-specific sensor signals; and
processing the windowed axis-specific sensor signals over said analysis interval to resolve the windowed axis-specific sensor signals into said components which are due to the plurality of source signals.

2. The magnetic positioning system of claim 1 wherein each of the source signals has a frequency such that it has a number of cycles, x, in the period, T, wherein $1 \leq x \leq 50$.

3. The magnetic positioning system of claim 2 wherein $3 \leq x \leq 25$.

4. The magnetic positioning system of claim 2 wherein each of the source signals has a frequency in a range from 1 Hz to 500 Hz.

5. The magnetic positioning system of claim 1 wherein the source signals have different frequencies, and wherein each of the source signals has a frequency such that it has an integer number of cycles in the period, T, such that the source signals are orthogonal to each other over the period, T.

6. The magnetic positioning system of claim 5 wherein the frequencies of the source signals are not multiples of one another.

7. The magnetic positioning system of claim 1 wherein the source signals are modulated with different orthogonal codes, such that the source signals are orthogonal to each other over the period, T.

8. The magnetic positioning system of claim 1 wherein two of the source signals have phases which differ by $$\frac{\pi}{2},$$

such that said two of the source signals are orthogonal to each other over the period, T.

9. The magnetic positioning system of claim 1 wherein the magnetic positioning system is configured to resolve the detected magnetic field into components which are due to the plurality of source signals once per update interval, and use the components to determine one or both of the position and the orientation of the multi-axis magnetic field sensor relative to the multi-axis magnetic field source once per update interval, wherein the update interval is shorter than the analysis interval.

10. The magnetic positioning system of claim 9 wherein the update interval is less than or equal to the period T.

11. The magnetic positioning system of claim 1 wherein the window function is a raised cosine function with a period of 2T, and wherein said analysis interval over which the windowed axis-specific sensor signals are processed is 2T.

12. The magnetic positioning system of claim 1 wherein the magnetic positioning system is configured to resolve the detected magnetic field into components which are due to the plurality of source signals once per update interval, and use the components to determine one or both of the position and the orientation of the multi-axis magnetic field sensor relative to the multi-axis magnetic field source once per update interval, wherein the update interval is shorter than the analysis interval, and wherein a respective window function is used for each update interval, such that the window functions are overlapping in time.

13. The magnetic positioning system of claim 1 wherein the multi-axis magnetic field source is configured to simultaneously excite each of the axes with a plurality of source signals, wherein all of the source signals with which all of the axes are excited are orthogonal to each other over the period, T.

14. The magnetic positioning system of claim 1 wherein the magnetic positioning system is configured to synchronise the timing of the multi-axis magnetic field source and the multi-axis magnetic field sensor with each other by:
providing an out-of-band time-reference signal to the multi-axis magnetic field source and to the multi-axis magnetic field sensor;
causing the multi-axis magnetic field source to excite one or more of its axes with a time-reference signal which has a period of 2T; or
causing the multi-axis magnetic field source to simultaneously excite one of its axes with two source signals which have no common periodicity in intervals which are submultiples of the period, T.

15. The magnetic positioning system of claim 1 comprising a plurality of multi-axis magnetic field sources and a plurality of multi-axis magnetic field sensors, wherein each of the multi-axis magnetic field sources are configured to generate a magnetic field by simultaneously exciting a plurality of axes of the multi-axis magnetic field source with respective source signals, wherein all of the source signals for all of the multi-axis magnetic field sources are orthogonal to each other over the period, T.

16. A robotic surgical system comprising:
a plurality of parts; and
the magnetic positioning system of claim 15,
wherein a respective one of the multi-axis magnetic field sources and a respective one of the multi-axis magnetic field sensors is secured to each of the parts.

17. The robotic surgical system of claim 16 wherein the magnetic positioning system is configured to:
for each of the parts, analyse the magnetic field detected at the multi-axis magnetic field sensor secured to that part to determine measurement information indicating one or both of the position and the orientation of that multi-axis magnetic field sensor relative to the multi-axis magnetic field sources secured to a plurality of the other parts; and
determine the positions and/or orientations of the parts in the robotic surgical system using: (i) pre-determined information indicating, for each of the parts, the positions and orientations on that part at which the multi-axis magnetic field source and the multi-axis magnetic field sensor are secured, and (ii) the determined measurement information for each of the parts.

18. The robotic surgical system of claim 17 wherein the magnetic positioning system is configured to also use known geometrical arrangements of the parts of the robotic surgical system to determine the positions and/or orientations of the parts in the robotic surgical system.

19. A magnetic positioning method for use in a robotic surgical system, the magnetic positioning method comprising:
generating a magnetic field by simultaneously exciting a plurality of axes of a multi-axis magnetic field source with respective source signals that are orthogonal to each other over a period, T;

detecting the generated magnetic field at a multi-axis magnetic field sensor by determining, for each of a plurality of axes of the multi-axis magnetic field sensor, an axis-specific sensor signal representing the detected magnetic field for that axis;

analysing the detected magnetic field by processing the axis-specific sensor signals over an analysis interval which is at least as long as the period, T, to resolve the axis-specific sensor signals into components which are due to the plurality of source signals; and using the components to determine one or both of the position and the orientation of the multi-axis magnetic field sensor relative to the multi-axis magnetic field source, wherein said processing the axis-specific sensor signals comprises:

multiplying the axis specific sensor signals by a window function to determine windowed axis-specific sensor signals; and processing the windowed axis-specific sensor signals over said analysis interval to resolve the windowed axis-specific sensor signals into said components which are due to the plurality of source signals.

\* \* \* \* \*